(12) United States Patent  (10) Patent No.: US 8,162,663 B2
Lombardi  (45) Date of Patent: Apr. 24, 2012

(54) DENTAL IMPLANT

(76) Inventor: Steven Lombardi, New Castle, PA (US)

( * ) Notice: Subject to any disclaimer, the term of this patent is extended or adjusted under 35 U.S.C. 154(b) by 90 days.

(21) Appl. No.: 12/601,257

(22) PCT Filed: Feb. 6, 2008

(86) PCT No.: PCT/US2008/053120
§ 371 (c)(1),
(2), (4) Date: Nov. 21, 2009

(87) PCT Pub. No.: WO2009/002570
PCT Pub. Date: Dec. 31, 2008

(65) Prior Publication Data
US 2010/0167241 A1   Jul. 1, 2010

Related U.S. Application Data

(60) Provisional application No. 60/945,665, filed on Jun. 22, 2007.

(51) Int. Cl.
A61C 8/00 (2006.01)
A61C 5/00 (2006.01)

(52) U.S. Cl. .................................... 433/174; 433/215
(58) Field of Classification Search .......... 433/172–176, 433/201.1, 215; 623/16.11
See application file for complete search history.

(56) References Cited

U.S. PATENT DOCUMENTS

| 5,026,280 A * | 6/1991 | Durr et al. ............... 433/175 |
| 6,283,753 B1 | 9/2001 | Willoughby |
| 2003/0013068 A1 * | 1/2003 | Gittleman ................ 433/173 |
| 2004/0006346 A1 | 1/2004 | Holmen |
| 2004/0142304 A1 * | 7/2004 | Cottrell ................... 433/173 |

* cited by examiner

Primary Examiner — Heidi M Eide
(74) Attorney, Agent, or Firm — James R. Williams

(57) ABSTRACT

A method of fixing a dental implant assembly is described. The assembly includes an implant, a driver/abutment device, and a spacer. The bottom portion of the device has a protrusion with an inferior aspect and a superior aspect. The spacer prevents the oversized, superior aspect of the device from engaging an interior cavity of the implant so that the driver is easily removable after insertion of the implant in the jaw of a patient. Removing the spacer permits the superior aspect to engage the interior cavity, thereby permanently fixing the driver to the implant.

2 Claims, 2 Drawing Sheets

DENTAL IMPLANT

This application is a national phase application filed under 35 U.S.C. 371 of international application No. PCT/US08/53120 filed on Feb. 6, 2008 claiming benefit under 35 U.S.C. 119(e) of U.S. provisional application No. 60/945,665, filed Jun. 22, 2007 which is incorporated by reference.

FIELD OF THE INVENTION

The invention relates to a dental implant and more specifically to a dental implant comprising a spacer that permits a single device to function as both a driver and an abutment for dental implants.

BACKGROUND OF THE INVENTION

Dental implants serve as foundations for a variety of dental prostheses, including crowns and bridges. Although implants may be made in a variety of forms, a conventional implant has a generally cylindrical body that is externally threaded, and is surgically fixed into the patient's healthy bone tissue. The implant also includes a top portion comprising a cavity having an internal thread, and a structure adapted to receive an insertion tool. The insertion tool engages the top portion and facilitates insertion of the implant into the bone. Insertion often includes rotating the implant so that the external threads pull the implant into the bone. The insertion tool is removed from the implant after insertion. The implant may even include an external coating, such as hydroxyapatite or a titanium plasma spray, which enables bone tissue to integrate better with the implant, thereby providing enhanced support for the prosthesis.

A surgeon prepares the implant site by first incising the gingival tissue at the implant site and then drilling a substantially cylindrical bore into the bone mass. The surgeon positions the implant over the bore and screws the externally threaded implant into the bone tissue. The surgeon typically uses a ratcheting or rotating tool to screw the implant into the bone. The ratcheting tool may directly engage the implant but, for convenience, the ratcheting tool often imparts torque to a driver that is removably secured to the top portion of the implant. The driver transmits the torque to the implant. The driver includes a bottom portion that is configured to matingly engage the top end of the implant. The implant and driver may be secured together by a retaining screw to form an assembly. The assembly facilitates delivery of the implant to the surgical site. After fixing the implant into the bone, the driver is removed from the implant and the surgical site is closed and allowed to heal after which the gingival tissue over the implant is incised to expose the implant. At this time, a permanent abutment is secured to the top end of the implant. Importantly, the abutment must not move relative to the implant. To this end, a fixation screw engages internal threads of the implant and fixes the abutment to the implant. The bottom portion of the abutment may include a Morse taper that cold welds the abutment to the implant as the fixation screw is tightened.

Examples of driver-less systems include U.S. Pat. No. 4,960,381 to Niznick and U.S. Pat. No. 6,464,500 to Popovic. Niznick teaches a dental implant having an externally threaded surface and an internal structure for engaging an insertion tool. The top end of the implant is open and in registry with an internally-threaded portion. The top end also includes a hex-shaped cavity in its inner wall surfaces for receiving a hex wrench. The internal hex-shaped configuration is intended to allow the insertion of the implant in the jawbone of a patient using an Allen-type wrench. Stress concentrations along the hex corners have resulted in numerous implant fractures.

Popovic describes a dental implant having an externally threaded surface and an internal structure for engaging an insertion tool. The top end of the implant includes an internally threaded portion. A hex-shaped cavity is located below the internally threaded portion for the purpose of receiving a hex wrench. The hex-shaped cavity is below the internally threaded portion, so the distance between corners of the hex-shaped cavity is smaller than the internally threaded portion. The hex-shaped cavity is therefore so small that at normal insertion torques, damage may occur to the insertion tool or the insert. As a result, the direct connection of the insert with the insertion tool is problematic.

Surgeons generally prefer systems that include drivers over systems that are driver-less. Drivers reduce stress concentrations while setting the implant and facilitate implantation by permitting the insertion tool to remain above the gum line. Driver-containing systems typically include an implant defining an internal cavity with a top end having a chamfered surface. The driver is removably fixed to the implant, such as with a retaining screw. The chamfered surface is of sufficient size and depth to afford lateral stability to any driver inserted into the cavity. The driver obviously increases the cost of the implant system.

The implant, driver, abutment, retaining screw, and fixation screw usually comprise titanium and are individually costly to produce. To reduce cost and complexity, manufacturers have attempted to use the driver as an abutment and the retaining screw as the fixation screw. Unfortunately, the driver must be removable from the implant but the abutment should be permanently fixed and immobile. Previous attempts to produce a single driver/abutment device have proven inadequate. While being used as a driver, the device can cold weld to the implant thereby negatively affecting removability. While being used as an abutment, the device can retain mobility thereby jeopardizing the prosthetic. A need exists for a driver/abutment device that is easily removable when setting the implant but fixedly secured when used as a permanent abutment.

SUMMARY OF THE INVENTION

The present invention describes a dental implant comprising an implant, a driver/abutment device, a fixation screw, and a spacer. The spacer permits the device to function as both a driver and an abutment without compromising the performance of either.

The device includes a bottom portion that matingly engages a top end of a dental implant. The dental implant defines a cavity communicating with the top end. The bottom portion of the device includes a protrusion having at least two aspects. An inferior aspect substantially conforms to at least a portion of the cavity. A superior aspect is slightly oversized relative the cavity. The spacer matingly engages the superior aspect of the implant. The spacer permits the inferior aspect to engage the cavity but prevents the superior aspect from engaging the cavity. In this configuration, the device can be used to fix the implant to a patient's bone but is still easily removed from the implant. Removing the spacer permits the superior aspect to engage the cavity. Tightening the device forces the oversized superior aspect against the cavity and effectively cold welds the device to the implant, thereby preventing further movement of the device relative to the implant.

In one embodiment, the device includes a protrusion comprising an inferior aspect and a superior aspect. The protrusion can have a polygonal cross-section, such as a substantially regular hexagon with substantially parallel pairs of walls. The walls of the superior aspect include a taper with about 3-5 degrees deviation. The implant includes a top end and defines a hexagonal cavity dimensioned to receive the inferior aspect. During setting of the implant, a spacer matingly engages the top end of the implant and prevents the superior aspect from engaging the hexagonal cavity. A surgeon may permanently fix the device to the implant by removing the spacer and securing the device to the implant.

In another embodiment, the implant includes a top end that matingly engages the driver/abutment device. The device includes a bottom portion comprising a protrusion having a plurality of aspects. The aspects include at least two different exterior dimensions. The implant defines an interior cavity having a threaded portion. The device is secured to the implant by a screw that passes through the device, through a spacer, and engages the threaded cavity. The spacer restricts any aspect of the protrusion from entering the cavity if the exterior dimension of the aspect exceeds the size of the interior cavity. The device is, therefore, removable from the implant. If the device is to be permanently and fixedly secured to the implant, the spacer is removed. With the spacer removed, the device is screwed to the implant. At least one aspect of the protrusion having an exterior dimension larger than the interior cavity is forced into the cavity, thereby cold welding the device to the implant and restricting their relative movement.

DETAILED DESCRIPTION OF THE INVENTION

Figure 1:
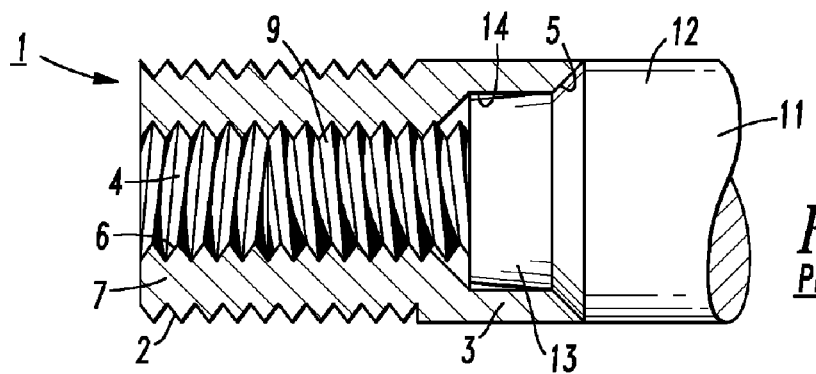
FIG. 1 shows a cross-section a first embodiment of a dental implant of the prior art.

FIG. 1 shows a dental implant assembly 1 of the prior art. An implant 7 includes a threaded exterior surface 2. The implant 7 defines an interior cavity 4 and includes a top end 3. The top end 3 may have a chamfer 5. The interior cavity 4 includes an interior threaded portion 6. A device 11 is secured to the implant 7 by a screw 9 that passes through the device 11 and engages the interior threaded portion 6 of the implant 7. The device 11 includes a bottom portion 12 having a protrusion 13. The protrusion 13 includes walls 14 that are substantially parallel to the interior cavity 4. Parallel walls 14 can facilitate removal of the device 11 from the interior cavity 4 after the implant 7 is fixed to a patient's bone. Unfortunately, parallel walls 14 permit relative movement of the device and the implant and, when used as an abutment, the device 11 should not move relative to the implant 7.

Figure 2:
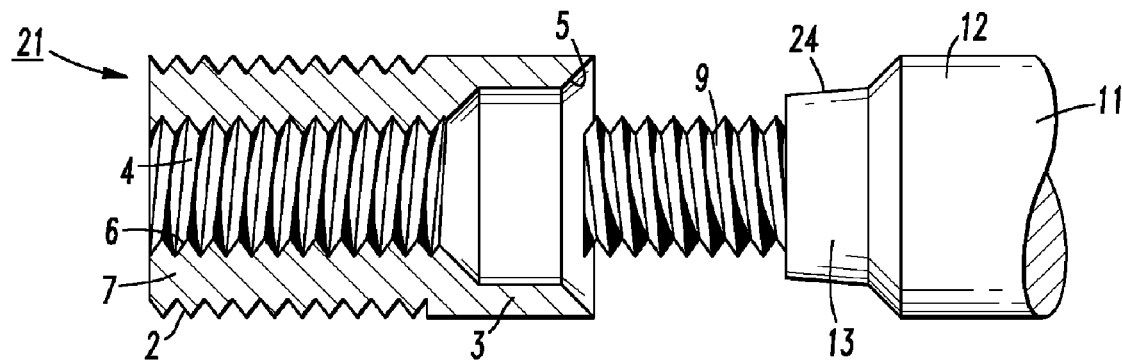
FIG. 2 shows a cross-section of a second embodiment of a dental implant of the prior art.

FIG. 2 shows a second dental implant assembly 21 of the prior art. This embodiment can overcome the problem of relative movement of the abutment and the implant. The assembly is similar to the implant of FIG. 1 except that the protrusion 13 includes tapered walls 24 that decrease in exterior dimension as the tapered walls 24 extend from the bottom portion 12. At least a section of the tapered walls 24 has an exterior dimension that is slightly larger than the interior cavity 4 of the implant 7. Fixing the device 11 to the implant 7 forces the protrusion into the interior cavity 4. The section of the protrusion that is larger than the interior dimension is pressed against the interior cavity and can cold weld to the implant 7. Cold welding refers to a force of adhesion between two metals that are tightly pressed together. One skilled in the art would appreciate that the strength of adhesion depends on several factors, including the flatness of the surface, the composition of the metals, and the cleanliness of the surfaces. Cold welding resists relative movement of the device 11 and the implant 7. In this prior art embodiment, cold welding can occur during fixation of the implant 7 and impair removal of the device 11. The device 11 must be removed from the implant 7 after fixation of the implant to the bone in order to close the gingival tissue and allow that patient to heal. Cold welding can make removal of the device 11 from the implant 7 very difficult and can even require removal of the fused assembly 21.

Figure 3:
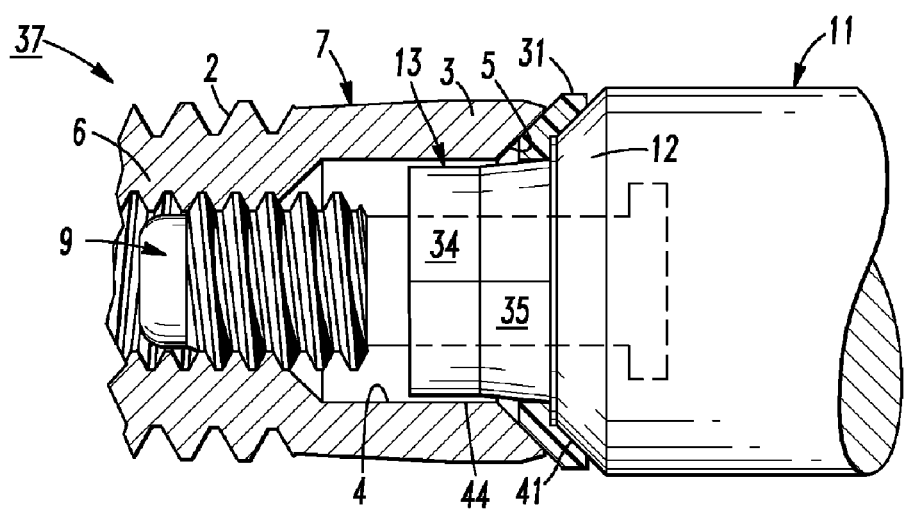
FIG. 3 shows a cross-section of an embodiment of the present invention.

The present invention describes a dental implant assembly 37 as shown in FIG. 3. The assembly permits the use of a single driver/abutment device that substantially avoids cold welding when used as a driver during fixation of the implant, and substantially reduces relative movement of the device and the implant when the device is used as an abutment. The driver/abutment device 11 includes a bottom portion 12 having a protrusion 13. The protrusion 13 includes at least two aspects, including an inferior aspect 34 and a superior aspect 35. The inferior aspect 34 substantially conforms to the interior cavity 4, preferably to an upper portion 44 of the interior cavity 4. The top end 3 generally comprises the upper portion 44, which is above the interior threaded portion 6. The superior aspect 35 includes a taper that diverges from inferior aspect 34 towards the bottom portion 12. At least a section of the superior aspect 35 has an exterior dimension larger than the interior cavity 4. During fixation of the implant 7 into bone, a spacer 31 matingly engages the top end 3 of the implant and the bottom portion 12 of the device 11. The spacer 31 prevents the superior aspect 35 from engaging the interior cavity 4 of the implant 7, and facilitates removal of the device 11 from the implant 7. When the device 11 is to be permanently fixed to the implant 7, the spacer 31 is removed and the superior aspect 35 engages the interior cavity 4. The superior aspect 35 can then cold weld to the interior cavity 4 of the implant 7, thereby reducing relative movement of the device 11 and the implant 7. The spacer 31 and the differing aspects of the protrusion permit a single device 11 to function effectively as both a driver and an abutment. As a driver, the device 11 is easily removable from the implant 7. As an abutment, the device 11 can cold weld to the implant 7 thereby restricting relative movement of the two elements.

The implant 7 of the present invention can include a threaded exterior surface 2. The implant 7 defines an interior cavity 4 and includes a top end 3. The top end 3 may have a chamfer 5. The interior cavity 4 includes an interior threaded portion 6. A device 11 is secured to the implant 7 by a fixation screw 9 that passes through the device 11 and engages the interior threaded portion 6 of the implant 7. The fixation screw 9 can secure the device 11 to the implant when the device 11 is used as either a driver or an abutment.

Figure 4:
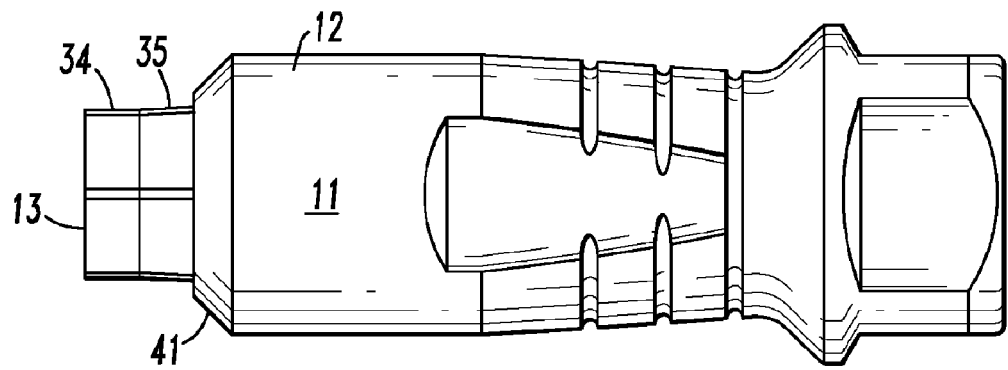
FIG. 4 shows a cross-section of a driver/abutment device of the present invention.

As shown in FIG. 4, the device 11 includes a bottom portion 12 having a protrusion 13 comprising an inferior aspect 34 and a superior aspect 35. The bottom portion 12 can also include a complementary chamfer 41 that preferable can complementary engage the chamfer 5 of the top end 3 of the implant 7. The protrusion will preferably have a length of at least about 0.7 mm and up to about 5.0 mm, and preferably between about 1.0 mm and about 2.0 mm. Greater length permits greater force to be transmitted between the device and the implant, but greater length also weakens the implant by hollowing out an increasingly large interior cavity. The inferior aspect and the superior aspect will typically be approximately the same length; however, either aspect may make up a majority of the length of the protrusion. The complementary chamfer 41 of the bottom portion 12 will preferably sealingly engage a top portion of an implant. Such an engagement increases the chance of cold welding the device to the implant in the absence of a spacer and prevents body fluids from leaking into the implant, thereby comprising its integrity.

Figure 5:
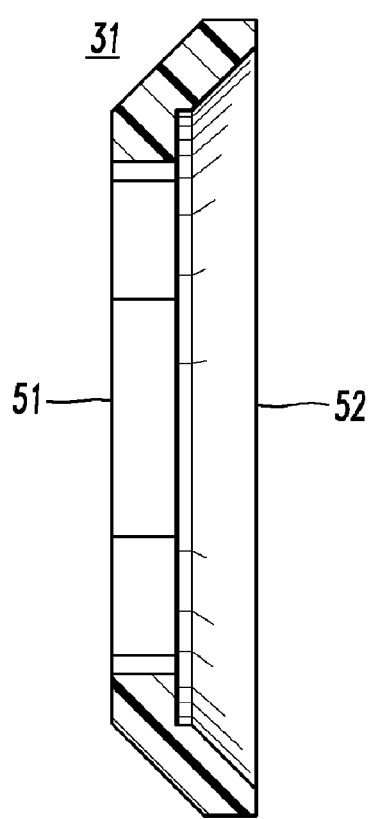
FIG. 5 shows a cross-section of a spacer of the present invention.

FIG. 5 shows a spacer 31. The spacer 31 includes an anterior face 51 that conforms substantially to the top end of the implant and a posterior face 52 that conforms substantially to the bottom portion of the device. Typically, the anterior face 51 and the posterior face 52 will be complementary.

For convenience of placement, the screw preferably unites the implant, spacer and device into a single assembly. A surgeon places the assembly into a prepared bore in a patient's mouth. An insertion tool transmits torque to the implant through the device and spacer, thereby screwing the implant into the bore and setting it into the bone. The spacer must permit transmission of torque from the insertion tool through the device to the implant while preventing the superior aspect of the protrusion from engaging the interior cavity of the implant. To this end, the spacer will matingly engage the top end of the implant and the bottom portion of the device. The top end may include a chamfer to facilitate engagement. The spacer can be sufficiently thick to prevent the superior aspect of the protrusion from engaging the interior cavity.

The spacer prevents the superior aspect of the protrusion from engaging the implant during insertion of the implant. Once the implant is set, the unit is disassembled by removing the fixation screw. The spacer can then be discarded. The device and implant can be permanently joined by placing the device on the implant and tightening the fixation screw. The standard of care in dentistry dictates permanent joining will occur after a period of healing. Without the spacer, tightening the screw forces the superior aspect of the protrusion into the interior cavity of the implant. The taper of the superior aspect can cold weld to the interior cavity and restrict relative movement of the device and the implant. A prosthetic tooth is then typically placed over the device to complete the restoration.

The implant, device and screw will comprise a suitable dental material, such as titanium. The spacer, being temporary, may comprise any suitable compression-resistant material. A compression-resistant material will resist compressive forces created by the fixation screw sufficiently to resist cold welding of the superior aspect to the interior cavity during the fixation step. The material must be sterilizable, preferably using gamma-irradiation. The material preferably has a low coefficient of friction and will not cold weld to either the implant or the device. Suitable materials include, for example, polymers, metals, and composites. Metals include traditional dental materials, such as stainless steel, titanium, or amalgams, but may also include brass and non-noble metals. Composites include materials comprising polymers and ceramic materials. In one embodiment, the spacer comprises a polymer having a low coefficient of friction such as, for example, polyolefins, nylons, fluorinated polymers and polyoxymethylene.

The implant typically includes an exterior surface having self-tapping threads and is usually not more than about 7 mm in diameter. The implant may have a length from about 5 mm to about 20 mm. The interior cavity of the implant should not allow rotation around an axis along the length of the implant; otherwise, the prosthesis that will be fixed to the device could rotate in the patient's mouth. To this end, the cavity will have a non-rotatable shape. Examples include polygons, such as hexagons or non-circular shapes. The cavity and the device will, therefore, define a non-rotatable mating surface.

The device includes a protrusion having at least two aspects. The inferior aspect should fit removably into the interior cavity of the implant. For example, where the interior cavity includes a hexagonal cross-section with parallel pairs of walls, the inferior aspect should also be hexagonal with similarly parallel walls. The superior aspect should be slightly oversized so that pressing the superior aspect into the cavity will prevent further movement. The superior aspect will often be tapered, such as, for example a Morse taper. A Morse taper aligns two bodies and restricts their relative movement. The taper may be of any convenient angle but the taper angle will commonly range up to 5 degrees and preferably from 3-5 degrees.

Numerous modifications and variations of the present invention are possible. It is, therefore, to be understood that within the scope of the following claims, the invention may be practiced otherwise than as specifically described. While this invention has been described with respect to certain preferred embodiments, different variations, modifications, and additions to the invention will become evident to persons of ordinary skill in the art. All such modifications, variations, and additions are intended to be encompassed within the scope of this patent, which is limited only by the claims appended hereto.

The invention claimed is:

1. A method of fixing a dental implant using a dental implant assembly comprising:
   a. implant defining an interior cavity;
   b. a device including a bottom portion comprising a protrusion, the protrusion including an inferior aspect and a superior aspect, the inferior aspect dimensioned to fit removably within the interior cavity, at least a section of the superior aspect is oversized relative to the interior cavity;
   c. a fixation screw that secures at least a portion of the protrusion in the interior cavity by the fixation screw passing through the device and engaging an interior threaded portion of the interior cavity; and
   d. a spacer separating the superior aspect of the protrusion from the interior cavity when the implant and the device are connected, and the spacer capable of being removed so that the superior aspect contacts the interior cavity,
   wherein the method includes (a) fixing the implant with the spacer between the implant and the device, and (b) securing the device to the implant by removing the spacer, placing the device on a top end of the implant, and tightening the fixation screw through the device and into the interior threaded portion.

2. The method of claim 1, wherein tightening the fixation screw creates a cold weld between the device and the implant.

* * * * *